(12) United States Patent
Mohan Rao et al.

(10) Patent No.: US 8,546,615 B2
(45) Date of Patent: Oct. 1, 2013

(54) SOLID DAPOXETINE

(75) Inventors: Dodda Mohan Rao, Hyderabad (IN);
Pingili Krishnareddy, Hyderabad (IN);
Aadepu Jithender, Hyderabad (IN)

(73) Assignee: Symed Labs Limited (IN)

( * ) Notice: Subject to any disclaimer, the term of this patent is extended or adjusted under 35 U.S.C. 154(b) by 0 days.

(21) Appl. No.: 13/509,725

(22) PCT Filed: Nov. 13, 2009

(86) PCT No.: PCT/IN2009/000640
§ 371 (c)(1),
(2), (4) Date: May 14, 2012

(87) PCT Pub. No.: WO2011/058572
PCT Pub. Date: May 19, 2011

(65) Prior Publication Data
US 2013/0150453 A1    Jun. 13, 2013

(51) Int. Cl.
*C07C 217/64* (2006.01)
*C07C 213/10* (2006.01)
*A61K 31/085* (2006.01)
*A61K 31/138* (2006.01)

(52) U.S. Cl.
USPC .......................... 564/352; 564/437; 514/650

(58) Field of Classification Search
None
See application file for complete search history.

(56) References Cited

U.S. PATENT DOCUMENTS 5,135,947 A    8/1992  Robertson et al.
5,292,962 A *  3/1994  Alt et al. .................. 568/633

FOREIGN PATENT DOCUMENTS

| CN | 1709859    |    | 12/2005 |
| CN | 1821212    |    | 8/2006  |
| CN | 101012147  | A  | 8/2007  |
| CN | 101367739  | A  | 2/2009  |
| KR | 2011051746 | A  | 5/2011  |
| WO | 2008035358 | A3 | 3/2008  |
| WO | 2011058572 | A2 | 5/2011  |

OTHER PUBLICATIONS

Feret, Formulary (2005), 40(7) p. 227-230.*
Merriam-Webster online dictionary, entry: solid, retrieved on Jun. 29, 2013 from the internet at <URL:http://www.merriam-webster.com/dictionary/solid>.*
International Search Report dated Jun. 28, 2012.
Oliver Torre, et al. Lipase-catalyzed resolution of chiral 1,3-amino alcohols: application in the asymmetric synthesis of (s)-dapoxetine, Tetrahedron: Asymmetry 17 (2006) 860-866.
Shafi A. Siddiqui and Kumar V. Srinivasan, Enantioselective Synthesis of (S)-dapoxetine, Tetrahedron, Asymmetry:18, (2007) 2099-2103.
Chincholkar, et al. An efficient formal synthesis of (S)-Dapoxetine from Enantiopure 3-hydroxyazetidin-2-one, Tetrahedron, (2009)65(12), p. 2605-2609.
William J. Wheeler and Douglas D. O'Bannon, A Chiral Synthesis of Dapoxetine Hydrochloride, a Serotonin Reuptake Inhibitor, and Its Cisotopomer, Journal of Labelled Compounds and Radiopharmaceuticals (1992)31(4), 305-15.
E Livi, et al. Synthesis of [11C]dapoxetine, HCI, a Serotonin Reuptake Inhibitor:biodistribution in Rat and Preliminary Pet imaging in the Monkey, Nuclear medicine and biology (1994), 21(4) 669-675.
Lin Li, et al. Isolation and Structural Elucidation of Dapoxetine as an Adulterant in a Health Supplement Used for Sexual Performance Enhancement, Journal of Pharmaceutical and Biomedical Analysis (2009), 50(5), 724-728.
Zhongguo Yiyao Gongye Zazhi, Preparation of 3-dimethylamino-3-phenylpropanol: Chinese Journal of Pharamaceuticals 2006, 37(3), 152-153 and Abstract.
Zhongguo Xinyao Zazhi, Synthesis of Dapoxetine, Chinese Journal of New Drugs, 2007), vol. 16, No. 2, 111-113 and Abstract.
K. Venkatesan, et al. A stereoselective Synthesis of (S)-dapoxetine starting from trans-cinnamyl alcohol, National Chemical Laboratory, Pune, India (Gainesville, FL U.S. (2008), (16), 302-310.
Zhongguo Xinyao Zazhi, Synthesis of Dapoxetine Hydrochloride, (2008), 17(24), 2119-2121 and Abstract.

* cited by examiner

*Primary Examiner* — Brian J Davis
(74) *Attorney, Agent, or Firm* — Caesar, Rivise, Bernstein, Cohen & Pokotilow, Ltd.

(57) ABSTRACT

The present invention relates to solid racemic dapoxetine, solid dapoxetine S(+)enantiomer, processes for their preparation and their use in the pharmaceutically active compound dapoxetine acid addition salt, and pharmaceutical compositions thereof.

24 Claims, 4 Drawing Sheets

SOLID DAPOXETINE

FIELD OF THE INVENTION

The present invention relates to solid racemic dapoxetine, solid dapoxetine S(+)enantiomer, processes for their preparation and their use in the pharmaceutically active compound dapoxetine acid addition salt, and pharmaceutical compositions thereof.

BACKGROUND OF THE INVENTION

Dapoxetine and its enantiomers are potent selective serotonine reuptake inhibitors (SSRIs) useful in the treatment of variety of diseases such as premature ejaculation, which is most common in men and other disorders like depression. Dapoxetine, a compound structurally related to the antidepressant fluoxetine (Prozac) is enantiomerically pure and one of the important drugs as an serotonin reuptake inhibitor. Dapoxetine is under phase III clinical trials in the United States, and it is approved as dapoxetine hydrochloride in various European countries for the indication of premature ejaculation and is marketed by Johnson & Johnson under the brand name PRILIGY. Dapoxetine hydrochloride is chemically described as (S)-N,N-dimethyl-3-(naphthalen-1-yloxy)-1-phenylpropan-1-amine hydrochloride (herein after referred by its generic name dapoxetine) which is represented by the structural formula:

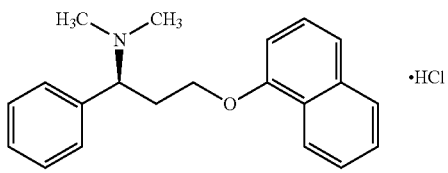 [SMILES: CN(C)[C@@H](CCOc1cccc2ccccc12)c1ccccc1 ; Cl]

European Patent No. 0,288,188 B1 (U.S. Pat. No. 5,135,947) describes 1-phenyl-3-napthalenyloxy propanamines derivatives including dapoexetine or a stereoisomer or a salt thereof, a pharmaceutical composition and method of treatment.

The EP'188 patent discloses a process for the preparation of enantiomerically pure S-(+)-dapoxetine as an oil and addition salts, by treating with inorganic acids such as hydrochloric acid, as well as, organic acids, such as oxalic acid, tartaric acid and p-toluene sulfonic acid.

U.S. Pat. No. 5,292,962 discloses a process for the preparation of S(+) dapoxetine and its acid addition salts by treating with inorganic acids such as hydrochloric acid.

Shafi A. Siddiqui et al Tetrahydron Asymmetry 17 (2006) 860-866 and Tetrahydron: Asymmetry 18 (2007) 2099-2103 describes a process for the preparation of S-(+)-dapoxetine as a colorless oil.

PCT application publication WO 2008035358A2 describes a process for the preparation of S(+) dapoxetine by resolution of racemic (±)-dapoxetine using (+)-di-p-toluoyl tartaric acid as a resolving agent to obtain S(+)-dapoxetine and its salts.

The aforementioned processes dealt only about the preparation of racemic dapoxetine and dapoxetine S(+)enantiomer in the form of an oil and as crude residues which are impure.

The discovery of solid states of intermediates of a pharmaceutically useful compound, like dapoxetine hydrochloride, provides an opportunity to improve the performance characteristics of a pharmaceutical product. Thus, it enlarges the repertoire of the materials that a formulation scientist has available for designing, for example, a pharmaceutical dosage form of a drug with a targeted release profile or other desired characteristic.

The racemic dapoxetine and dapoxetine S(+)enantiomer in the solid form is not reported in the art.

Now, racemic dapoxetine and dapoxetine S(+)-enantiomer as solids have been discovered.

The present invention relates to the solid state properties of racemic dapoxetine and dapoxetine S(+)enantiomer. These properties can be influenced by controlling the conditions under which racemic dapoxetine and dapoxetine S(+)enantiomer are obtained in solid form.

Solid state physical properties include, for example, the flowability, compaction and solubility, which eases the handling and processing of the final pharmaceutical product.

The solid form of a compound may also affect its behavior on compaction and its storage stability.

These practical physical characteristics are influenced by the conformation and orientation of molecules in the unit cell, which defines a particular polymorph of a compound which may give rise to distinct spectroscopic properties that may be detectable by XRPD, solid state $^{13}$C NMR spectroscopy, DSC and infrared spectrometry.

Additionally, types of multiple component solids that may potentially offer other property improvements for a pharmaceutical compound or salt thereof include for e.g., solvates) e.g., hydrates). See, e.g., Byrn et al., Solid state chemistry of drugs, supra.

The discovery of solid forms of intermediates of a pharmaceutically important product is of great importance in the development of a safe, effective, stable and marketable pharmaceutical compound.

Since the solid form of racemic dapoxetine and dapoxetinde S(+) enantiomer is obtained with high purity, it is hence more, suitable for pharmaceutically active compounds and their formulations. Also, the the solids will also will also be used to obtain highly pure pharmaceutically acceptable salts of dapoxetine.

Accordingly, there is thus an unmet need for solid forms of the intermediates, like racemic dapoxetine and dapoxetine S(+)enantiomer.

Now, we have invented and isolated racemic dapoxetine and dapoxetine S(+)enantiomer in solid forms which are obtained with high purity, and hence are more suitable for the preparation of the highly pure, final pharmaceutical product dapoxetine hydrochloride.

SUMMARY OF THE INVENTION

The present invention is directed to solid racemic dapoxetine, solid dapoxetine S(+) enantiomer, processes for their preparation and their use in the pharmaceutically active compound dapoxetine acid addition salt and pharmaceutical compositions thereof.

In one aspect, the present invention relates to solid racemic dapoxetine.

In another aspect, the present invention relates to a process for preparing solid racemic dapoxetine, comprising:
a) Providing a solution of racemic dapoxetine in hydrocarbon solvent n-hexane or cyclohexane or a mixture thereof; and
b) evaporating the solvent(s) or by cooling the solution obtained in step (a) to below about 30° C.; and
c) recovering the solid obtained in step (b) by conventional methods to afford the desired solid racemic dapoxetine.

In yet another aspect, the present invention relates to solid dapoxetine S(+) enantiomer.

In yet further aspect, the present invention relates to a process for preparing solid dapoxetine S(+) enantiomer, comprising:
  a) Providing a solution of dapoxetine S(+)enantiomer in hydrocarbon solvent n-hexane or cyclohexane or a mixture thereof; and
  b) Evaporating the solvent(s) or by cooling the solution obtained in step (a) to below about 30° C.; and
  c) Recovering the solid obtained in step (b) by conventional methods to afford the desired solid dapoxetine S(+) enantiomer.

In yet still further aspect, the present invention relates to use of solid racemic dapoxetine and solid dapoxetine S(+) enantiomer in the synthesis substantially optically pure dapoxetine or a pharmaceutically acceptable salt thereof.

In yet another aspect, the present invention relates to pharmaceutical compositions comprising substantially optically pure dapoxetine or a pharmaceutically acceptable salt thereof and at least a pharmaceutically acceptable excipient.

DETAILED DESCRIPTION OF THE INVENTION

Figure 1:
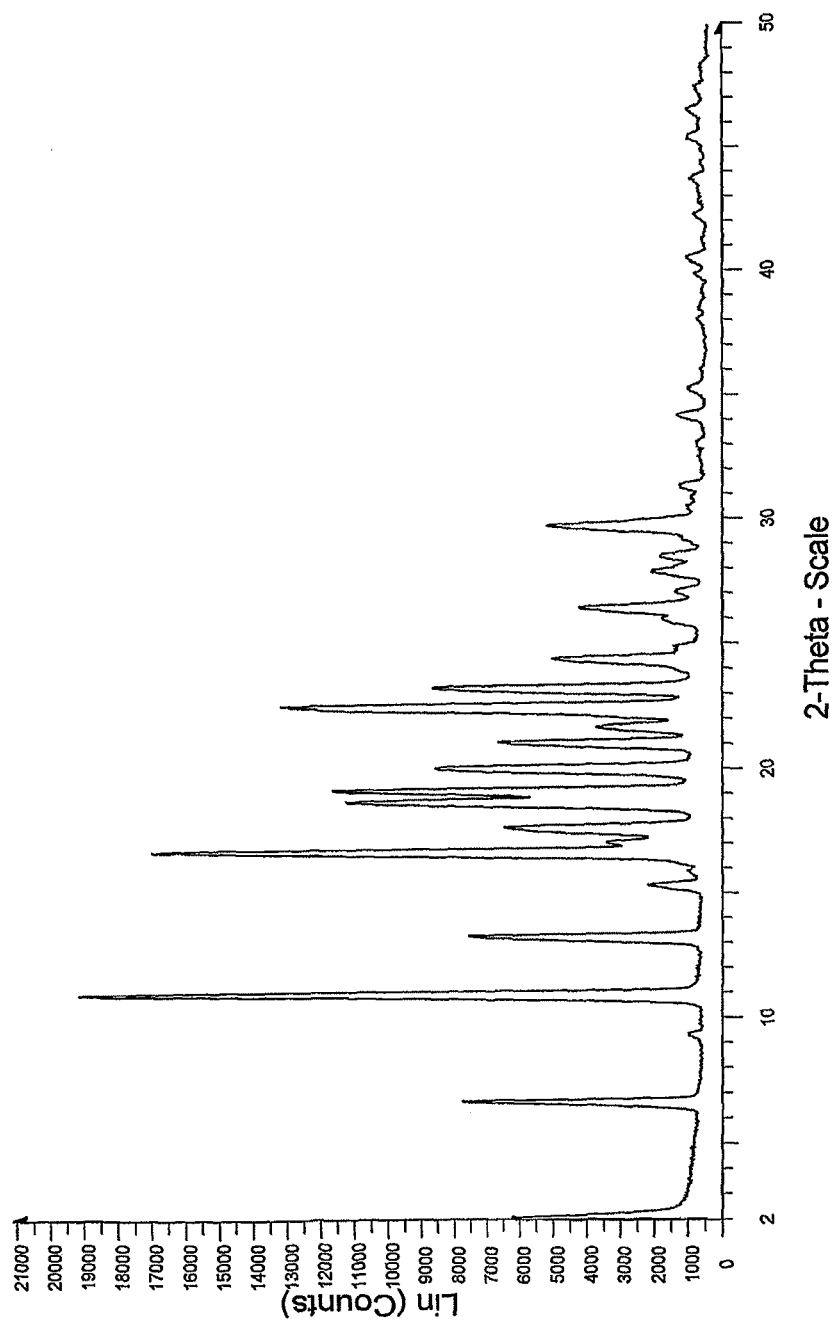
FIG. 1: illustrates a characteristic X-ray powder diffraction pattern of solid racemic dapoxetine.

The present invention is directed to solid racemic dapoxetine, solid dapoxetine S(+) enantiomer, processes for their preparation and their use in the pharmaceutically active compound dapoxetine acid addition salt and pharmaceutical compositions comprising them.

In one embodiment of the present invention, there is provided solid racemic dapoxetine.

In another embodiment, the present invention provides a process for preparing solid racemic dapoxetine, comprising:
  a) Providing a solution of racemic dapoxetine in hydrocarbon solvent n-hexane or cyclohexane or a mixture thereof; and
  b) evaporating the solvent(s) or by cooling the solution obtained in step (a) to below about 30° C.; and
  c) recovering the solid obtained in step (b) by conventional methods to afford the desired solid racemic dapoxetine.

The solution in step (a) is obtained by dissolving an oily residue or crude form of racemic dapoxetine or the racemic dapoxetine obtained from a reaction mixture, in a suitable organic solvent, including but not limited to hydrocarbons solvents, such as n-hexane, n-heptane, cyclohexane, toluene, xylene and the like or a mixture thereof. Other solvents that can dissolve the racemic dapoxetine of any form are also contemplated within the present invention.

When the salts of racemic dapoxetine are taken as starting materials, they are made in a slurry in water, basified, then extracted with suitable solvents, including but are not limited to, hydrocarbons solvents, like n-hexane or cyclohexane or a mixture thereof The volume of the solvent(s) used for dissolution of the racemic dapoxetine of any form depends on the solvent(s) and temperature used typically from about 1 to about 50 volumes on the weight of the compound taken. Preferably from about 2 to about 10 volumes.

The solution can be obtained at a temperature range from about 30° C. to about the boiling point of the solvent used. Preferably, at the boiling point of the solvent(s) used.

The time required to obtain an homogenous solution may depend on the volume of the solvent(s) used and the temperature. Typically, the suitable time period required to obtain a solution at a given temperature is from about 15 mins. to about 2 hours.

The solution obtained in step (a) is optionally filtered through celite or diatomous earth or hyflo material to separate the extraneous matter from the solution by conventional filtration techniques known in the art.

The solid is precipitated in step (b) by evaporation of the solvents from the solution at elevated temperatures under pressure or by cooling solution to below about 30° C., ranging from about −5° C. to about 30° C., preferably from about 0° C. to about 5° C.

The time period required for complete precipitation of the solid under cooling is typically from about 15 mins to about 5 hours, preferably from about 1 hour to about 4 hours.

The solid racemic dapoxetine obtained in step b) can be recovered by conventional methods known in the art for example filteration or centrifugation.

The solid racemic dapoxetine recovered may be further dried at a temperature ranging from about 25° C. to about 45° C. under reduced pressure, preferably from about 30° C. to about 40° C. under reduced pressure.

The solid racemic dapoxetine obtained may be dried in, for example a vacuum tray dryer, rotocon vacuum dryer, vacuum paddle dryer or pilot plant rotavapor, to further lower the residual solvents. When implemented, the preferred instrument is a vacuum tray dryer.

The solid racemic dapoxetine obtained herein above is optionally recrystallized from a solvent or a mixture of solvents, including but not limited to solvents selected from the group consisting of esters, such as ethyl acetate, butyl acetate, isopropyl acetate and the like; alcohols, such as methanol, ethanol, isopropanol and the like, or a mixture thereof. Alcohols alone, or in combination with water in any proportion, can also be used.

In yet another embodiment of the present invention, there is provided solid dapoxetine S(+) enantiomer.

In yet a further embodiment, the present invention provides a process for preparing solid dapoxetine S(+) enantiomer, comprising:
  a) providing a solution of dapoxetine S(+)enantiomer in a hydrocarbon solvent such as n-hexane or cyclohexane or a mixture thereof; and
  b) evaporating the solvent(s), or by cooling the solution obtained in step (a), to below about 30° C.; and
  c) recovering the solid obtained in step (b) by conventional methods to afford the desired solid dapoxetine S(+) enantiomer.

The solution in step (a) is obtained by dissolving an oily residue or crude form of dapoxetine S(+)enantiomer or the dapoxetine S(+) enantiomer obtained from a reaction mixture in suitable organic solvents, including but not limited to hydrocarbons solvents, such as n-hexane, n-heptane, cyclohexane, toluene, xylene and the like, or a mixture thereof. Other solvents that can dissolve the dapoxetine S(+) enantiomer of any form are also contemplated within the present invention.

When the salts of dapoxetine S(+)enantiomer are taken as starting materials, they are made in a slurry in water, basified, then extracted with suitable solvents including but not limited to hydrocarbons solvents, such as n-hexane or cyclohexane, or a mixture thereof The volume of the solvent(s) used for dissolution of the dapoxetine S(+) enantiomer of any form depends on the solvent(s) and temperature used, typically from about 1 to about 50 volumes on the weight of the compound taken, preferably from about 2 to about 10 volumes.

The solution can be obtained at a temperature range from about 30° C. to about the boiling point of the solvent used, preferably, at boiling point of the solvent(s) used.

The time required to obtain an homogenous solution may depend on the volume of the solvent(s) used and the temperature. Typically, the suitable time period required to obtain a solution at a given temperature is from about 15 mins. to about 2 hours.

The solution obtained in step (a) is optionally filtered through celite or diatomous earth or hyflo material to separate the extraneous matter from the solution by conventional filtration techniques known in the art.

The solid is precipitated in step (b) by evaporation of the solvents from the solution at elevated temperatures under pressure or by cooling solution to below about 30° C., ranging from about −5° C. to about 30° C., preferably from about 0° C. to about 5° C.

The time period required for complete precipitation of solid undercooling is typically from about 15 mins to about 5 hours, preferably from about 1 hour to about 4 hours.

The solid dapoxetine S(+) enantiomer obtained in step b) can be recovered by conventional methods known in the art for example, filtration or centrifugation.

The solid dapoxetine S(+) enantiomer recovered may be further dried at a temperature ranging from about 25° C. to about 45° C. under reduced pressure, preferably from about 30° C. to about 40° C. under reduced pressure.

The solid dapoxetine S(+) enantiomer obtained may be dried in, for example a vacuum tray dryer, rotocon vacuum dryer, vacuum paddle dryer or pilot plant rotavapor, to further lower the residual solvents. When implemented, the preferred instrument is a vacuum tray dryer.

The solid dapoxetine S(+) enantiomer obtained herein above is optionally recrystallized from a solvent or a mixture of solvents including but not limited to solvents selected from the group consisting of esters, such as ethyl acetate, butyl acetate, isopropyl acetate and the like; alcohols, such as methanol, ethanol, isopropanol and the like, or a mixture thereof. Alcohols alone, or in combination with water in any proportion, can also be used.

Advantageously, the solid racemic dapoxetine obtained herein has a purity greater than about 99 area %, preferably greater than about 99.5 area %, more preferably greater than about 99.9 area %, and most preferably greater than about 99.95 area %, as determined by HPLC.

Advantageously, the solid dapoxetine S(+)-enantiomer obtained herein has a purity of greater than about 99% e.e, preferably greater than about 99.5% ee, more specifically greater than about 99.9% e.e, and most specifically, greater than about 99.95% e.e, as determined by chiral HPLC The solid racemic dapoxetine of the present invention is stable at below about 45° C. for any period of time.

The solid dapoxetine S enantiomer of the present invention is stable at below about 60° C. for any period of time.

The processes reported for racemic dapoxetine and its S(+) enantiomer were never isolated in solid form.

The processes reported for the preparation of racemic dapoxetine and dapoxetine S(+)-enantiomer in the art yielded either in the form of oil or crude residue which are of impure form and may need multiple purifications to make it to the purities of about 99% so as to get the final product dapoxetine or its salt in purities to comply the regularity (ICH) acceptance, as they cannot be removed or washable in the final product, i.e., dapoxetine or its acid addition salt, preferably the hydrochloride salt.

Thus, the present invention avoids the further purification steps by isolation of solid racemic dapoxetine and solid dapoxetine S(+)enantiomer which can be used directly in the preparation of dapoxetine or its salt and can result in the final product with a high yield and purity.

As the solids of racemic dapoxetine and its S(+) enantiomer have not been isolated in solid form as of date of the present invention in particular to the isolated solid forms of racemic dapoxetine and its S(+) enantiomer.

As used herein, unless indicated otherwise, the term isolated, in reference to solid dapoxetine or its crystalline form, corresponds to racemic dapoxetine or its S(+)enantiomer that is physically separated from the reaction mixture, where they are formed.

The solid racemic dapoxetine and solid dapoxetine S(+) enantiomer of the present invention can be amorphous or crystalline. Moreover, it can be in the form of a hydrate or solvate. Preferably, the above solid racemic dapoxetine and its S(+) enantiomer are isolated in anhydrous crystalline forms.

The solid racemic dapoxetine of the present invention is characterized by XRPD and is substantially the same as depicted in FIG. 1.

Figure 2:
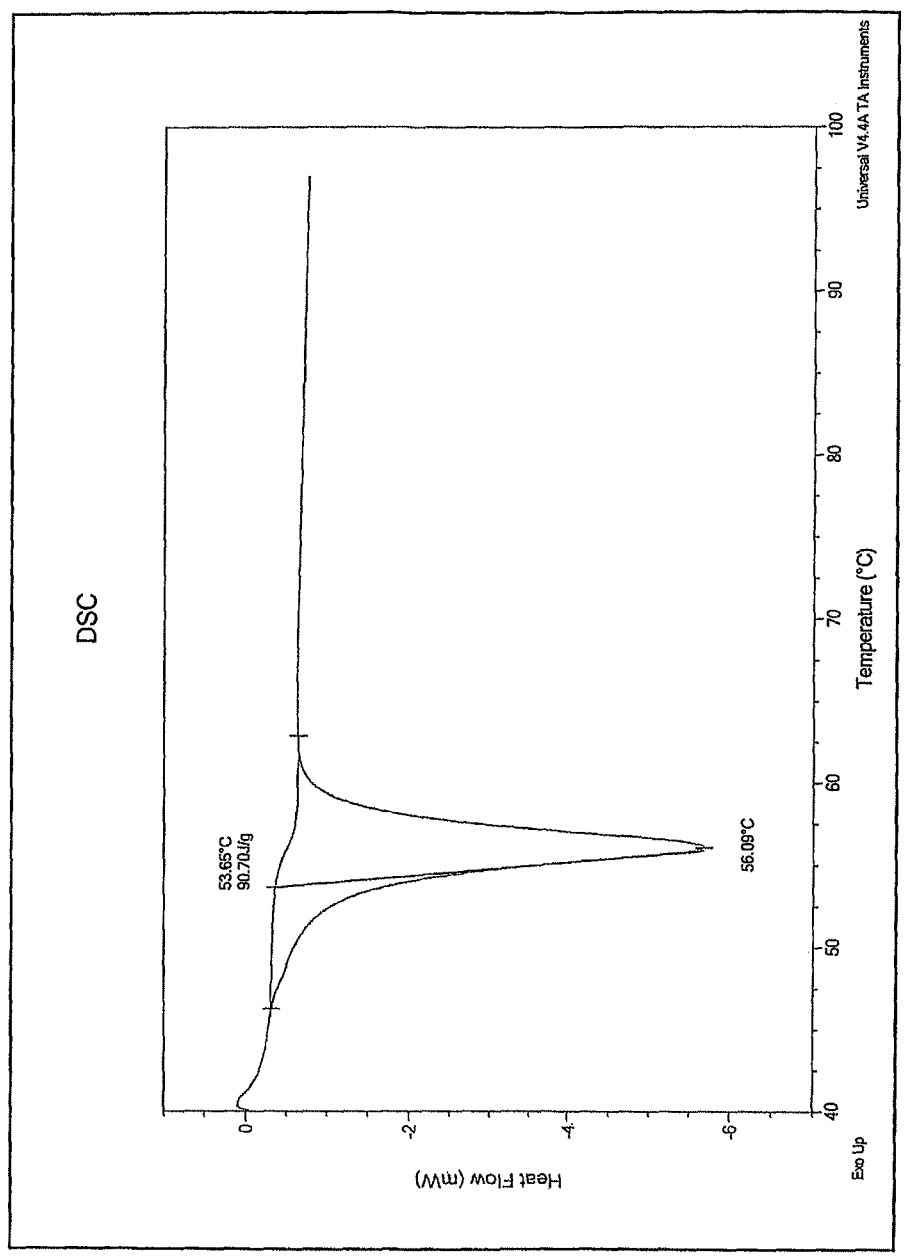
FIG. 2: illustrates a characteristic Differential scanning calorimetry (DSC) profile of solid racemic dapoxetine.

The solid racemic dapoxetine of the present invention is further characterized by Differential Scanning calometry (DSC) and is substantially same as depicted in FIG. 2.

Figure 3:
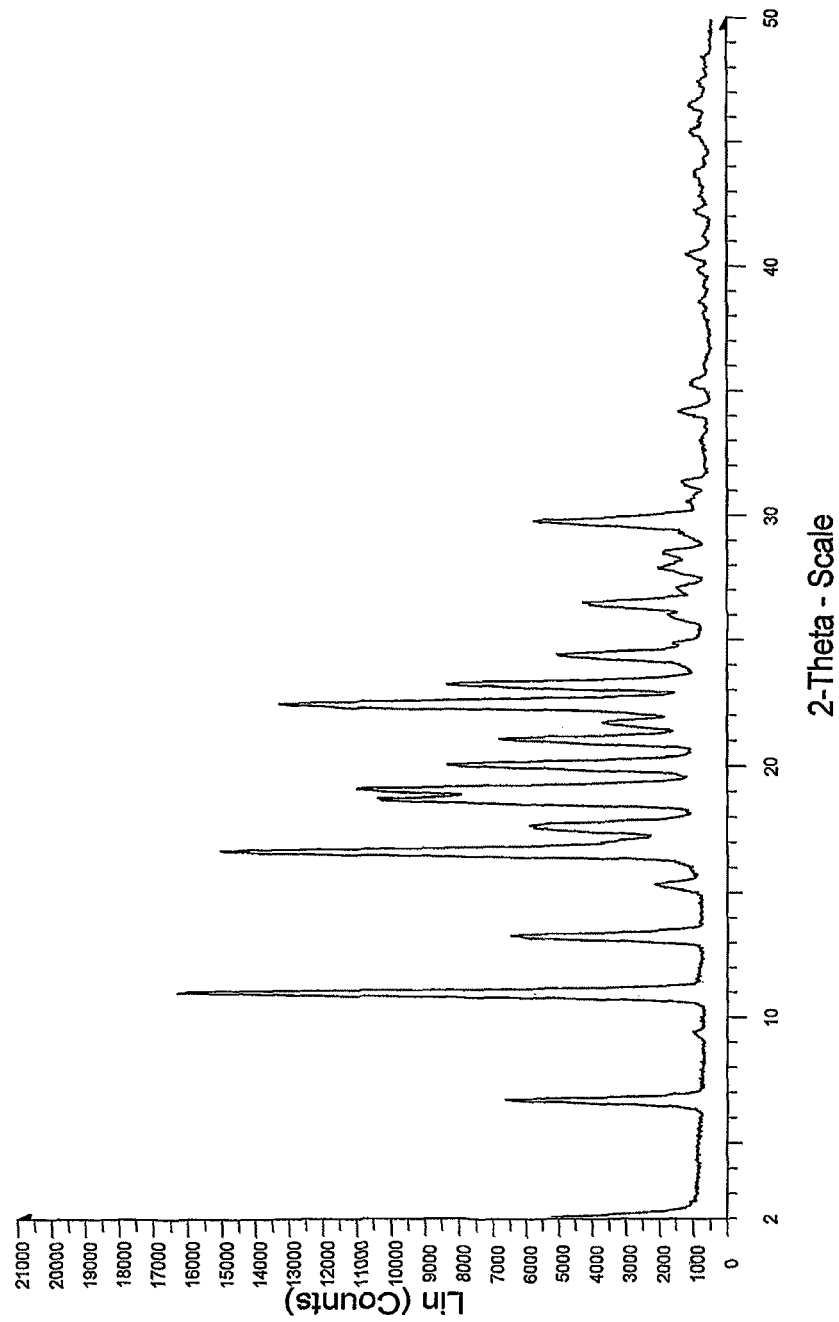
FIG. 3: illustrates a characteristic X-ray powder diffraction pattern of solid dapoxetine S(+)enantiomer.

The solid dapoxetine S(+)enantiomer of the present invention is characterized by XRPD and is substantially the same as depicted in FIG. 3.

Figure 4:
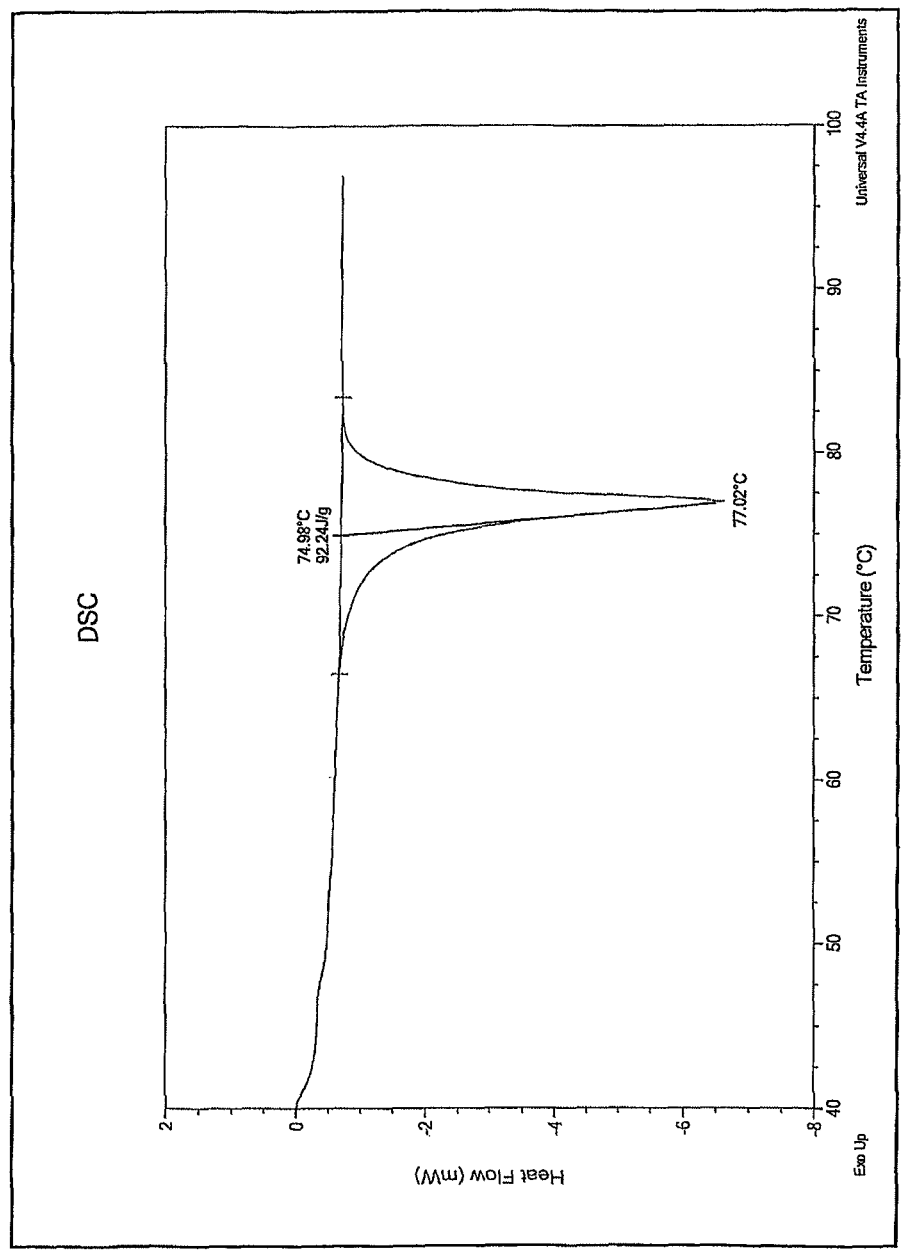
FIG. 4: illustrates a characteristic Differential scanning calorimetry (DSC) profile of solid dapoxetine S(+) enantiomer.

The solid dapoxetine S(+)enantiomer of the present invention is further characterized by Differential Scanning calorimetry (DSC) and is substantially the same as depicted in FIG. 4

In certain embodiments, solid forms provided herein are crystal forms, including, but not limited to, crystal forms of the salts of racemic dapoxetine and dapoxetine S(+) enantiomer.

In certain embodiments, the crystal forms are solvated (e.g., hydrated). Without intending to be limited by any particular theory, particular properties (e.g., storage stability, compressibility, bulk density or dissolution properties) of solid forms described herein are believed to be beneficial for manufacturing, formulation, storage and/or bioavailability of final compound dapoxetine hydrochloride salt. The said solids of the present invention are useful intermediates for preparing pharmaceutically acceptable salts of racemic dapoxetine and dapoxetine S(+)enantiomer.

Suitable acid addition salts which may include those formed with pharmaceutically acceptable organic or inorganic acids and are well known to those of skill in the art. Acids commonly employed to form such salts include inorganic acids such as hydrochloric, hydrobromic, hydroiodic, sulfuric and phosphoric acid, as well as organic acids such as para-toluenesulfonic acid, methanesulfonic, oxalic, para-bromophenyl sulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propionate, oxalate, malonate, succinate, suberate, sebacate, fumarate, maleate, butyne-1,4-dionate, hexyne-1,6-dioate, benzoate, chlorobenzoate, methylbenzoate, dinitrobenzoate, hydroxynenzoate, methoxybenzoate, phthalate, terephthalate, sulfonate, xylenesulfonate, phenylacetate, phenylpropionate, phenylbutyrate, citrate, lactate, hydroxybutyrate, glycollate, maleate, tartarate, methanesulfonate, propanesulfonantes, napthalene-1-sulfonate, naphthanlene-2-sulfonate, mandelate and the like salts. Preferred pharmaceutically acceptable acid addition salts include those formed with mineral acids such as hydrochloric acid and hydrobromic acid, and those formed with organic acids such as oxalic acid and maleic acid. A pharmaceutically preferred acid addition salt is the hydrochloride.

A preferred salt according to the present invention is (+)-dapoxetine di-p-toluoyl tartarate, which is useful as an intermediate for preparing the free base or another acid addition salt as appropriate.

The term "pharmaceutically acceptable salts" refers to salts prepared from a pharmaceutically acceptable acid, as known in the art. Examples herein, suitable acids and methods for preparing and analyzing salts are provided, e.g., in Handbook of Pharmaceutical Salts: Properties. Selection and Use. P. H. Stahl and C. G. Wermuth, Eds., (2002), Wiley, Weinheim;

Solid forms may be crystalline, amorphous or a mixture thereof. A "single-component" solid form comprising compound racemic dapoxetine consists essentially of compound racemic dapoxetine. This also applies to solid dapoxetine S(+)enantiomer.

The term "crystalline" and related terms when used to describe a substance, modification, material, component or product means the substance, modification, material, component or product is substantially crystalline as determined, e.g., by X-ray diffraction.

The term "crystal forms" and related terms refer to solid forms that are crystalline.

The term "enantiomerically pure" refers to a compound containing at least 75% of the named enantiomer out of the total amount of the two possible enantiomers contained therein. In a particular embodiment, "enantiomerically pure" refers to a compound containing at least 90% of the named enantiomer out of the total amount of the two possible enantiomers contained therein. In a more particular embodiment, "enantiomerically pure" refers to a compound containing at least 95% of the named enantiomer out the total amount of the two possible enantiomers contained therein. In a yet further embodiment, "enantiomerically pure" refers to a compound containing at least 97% of the named enantiomer out the total amount of the two possible enantiomers contained therein. In still yet a further embodiment, "enantiomerically pure" refers to a compound containing at least 98% of the named enantiomer out the total amount of the two possible enantiomers contained therein. In a further embodiment, "enantiomerically pure" refers to a compound containing at least 99% of the named enantiomer out the total amount of the two possible enantiomers contained therein.

The term isolated means that a particular solid form, e.g., crystal form, has been substantially physically separated from the medium from which it was created.

Solid forms provided herein may also comprise unnatural proportions of atomic isotopes at one or more of the atomic positions in solid racemic dapoxetine and solid dapoxetine S-enantiomer. For example, the compound may be substituted at one or more positions with isotopes, such as, for example, deuterium ($^2$H), tritium ($^3$H), or carbon-14 ($^{14}$C), carbon-13 ($^{13}$C) and isotopes of O and N. All isotopic variations of racemic dapoxetine and dapoxetine S-enantiomer, whether radioactive or not, are intended to be encompassed within the scope of the embodiments provided herein.

Solid forms comprising racemic dapoxetine and dapoxetine S-enantiomer can be prepared by the methods described herein, including the methods described in the Examples below, or by techniques including, but not limited to, heating, cooling, freeze drying, lyophilization, spray drying, quench cooling the melt, rapid solvent evaporation, slow solvent evaporation, solvent recrystallization, antisolvent addition, slurry recrystallization, crystallization from the melt, desolvation, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation and precipitation from a supercritical fluid. Unless otherwise specified, methods involving solvents described herein contemplate the use of any suitable common laboratory solvent, as known in the art.

While not intending to be bound by any particular theory, certain solid forms are characterized by properties, such as, for example, stability, solubility, dissolution rate, bioavailability and biological activity, appropriate for use as clinical and therapeutically active ingredients. Moreover, while not wishing to be bound by any particular theory, certain solid forms are characterized by properties, such as, for example, density, compressibility, hardness, morphology, powder flow, cleavage, stickiness, compaction, water uptake, electrical properties, thermal behavior, solubility, dissolution, solid-state reactivity, physical stability, chemical stability, and excipient compatibility that affect processes, such as, for example, yield, filtration, washing, drying, milling, mixing, tableting, formulation, storage, lyophilization, and other processing that make certain solid forms suitable for use in a solid dosage form. Such properties can be assessed using the particular analytical chemical techniques described herein or by methods known in the art.

In particular embodiments, solid forms described herein showed advantageous properties including properties relating to solubility, dissolution, solid-state reactivity, physical stability, and/or chemical stability.

In particular embodiments, techniques suitable for characterizing solid forms provided herein include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy.

In particular embodiments, solid forms provided herein have different physical properties such as, for example, melting temperatures, heats of fusion, solubilities, dissolution rates and/or vibrational spectra, as a result of, e.g., the arrangement or conformation of the molecules and/or ions in the solid forms.

The solid racemic dapoxetine and solid dapoxetine S(+) enantiomer of the present invention are characterized by X-ray powder diffraction measured on a bruker axs D8 advance X-ray powder diffractometer having a copper-Kα radiation ($\lambda$=1.54184 A°). Approximately 1 gm of sample was gently loaded on a sample cup and scanned from 2 to 50 degrees two-theta, at step size 0.03 degrees to theta per step and a step time of 38 seconds, scan speed 0.4 sec., scn mode:

continuos scan; scna type: locked coupled; goniometer type: Lynx Eye. The sample was simply placed on the sample holder. The sample was rotated at 30 rpm at a voltage of 40 KV and a current of 35 mA.

The solid racemic dapoxetine and solid dapoxetine S(+)-enantiomer of the present invention are further characterized by DSC (Differential Scanning calorimetry) measurements with a DSC Q200 (TA Instruments, Inc.).

About 1 to 1.3 mg of the powder was placed in an open aluminum pan and it was crimped with an aluminum lid. The crimped sample was then placed in the DSC cell opposite to an empty aluminum pan (as a reference) and the sample was scanned at 10 deg C./min from 40 deg C. to 100 deg C.

The solid racemic dapoxetine of the present invention was analysed by HPLC (high performance liquid chromatography) with method details as given below:

Chromatographic System:
   Column: Inertsil ODS 3V 250×4.6 mm; 5 μm or equivalent
   Detector: 215 nm.
   Flow Rate: 1.5 mL/min.
   Injection Volume: 10 μL
   Oven Temperature: 45° C.
   Run time: 80.00 min.
   Note: Run Standard solution up to 45 minutes using Mobile Phase-A.
   Diluent: Methanol
   Rinse Solvent: Methanol
   Auto Injector Parameters:
   Rinse Dip Time: 60 seconds
   Rinsing Injection volume: 2000 μL
   Rinsing Mode: Before and After aspiration
   Preparation Buffer (pH of the Buffer is Sensitive)
   Weigh about 1.36 g of Potassium dihydrogen phosphate and 1.74 g of Dipotassium hydrogen phosphate in to a beaker with 1000 mL water, mix the contents well.
   And adjust the pH of the solution to 6.0(±0.02) with dilute ortho phosphoric acid.
   Preparation Mobile Phase
   Prepare mixture of Buffer, Acetonitrile and Methanol in the ratio of 43:40:17 v/v/v respectively.
   Mix and pass through membrane filter (0.45 μm).
   Diluent Preparation:
   Use Methanol as diluent.
   Standard Stock Solution Preparation:
   Weigh about 25.0 mg of each Dapoxetine Hydrochloride working standard into a 100 mL volumetric flask.
   Dissolve and dilute the volume with diluent.
   Pipette out 5 mL of above solution in to a 100 mL volumetric flask. Dilute to the volume with diluent.
   Standard Solution Preparation:
   Pipette out 2.0 mL of standard stock solution in to a 50 mL volumetric flask. Dilute to the volume with diluent.
   Test Solution: (Prepare in Duplicate)
   Weigh about 25.0 mg of the test sample and transfer into a 50 mL volumetric flask.
   Dissolve and dilute the volume with diluent.
   Procedure:
   Equilibrate the column and system at 1.5 mL/min initial flow rate.
   Keep the data processor in area normalization mode.
   Inject diluent as blank twice into the system and record the chromatogram.
   Program the data processor to inhibit the peaks due to blank.
   Inject Standard solution for six times into the system and record the chromatograms.
   Inject each test solution into the system and record the chromatogram.
   Inject Standard solution into the system as online standard and record the chromatogram.

2. Chiral Purity by HPLC:
   Column: Chiralcel OJ-3; 150 mm×4.6 mm, 3 μm or Equivalent
   Detector Wavelength: 290 nm
   Flow rate: 1.0 mL/min.
   Injection Volume: 10 μL
   Column Temperature: 25° C.
   Run time: 15 min
   Diluent: Mobile phase
   Mobile Preparation:
   Take 900 mL of methanol, 100 mL of Ethanol and 1.0 mL of Di ethyl amine into a 1000 mL beaker. Mix the contents and pass through membrane filter (0.45 μm).
   Resolution Solution:
   Weigh accurately about 10.0 mg of Racemic Mixture and transfer in to a 20 mL volumetric flask containing 10 mL of mobile phase.
   Dissolve and dilute to the volume with mobile phase.
   Test Solution Preparation:
   Weigh accurately about 10.0 mg of Dapoxetine Hydrochloride test sample and transfer in to a 20 mL volumetric flask containing 10 mL of mobile phase.
   Dissolve and dilute to the volume with mobile phase.
   Procedure:
   Equilibrate the system with a flow rate of 1.0 mL/min.
   Keep the data processor in Area Percent mode and inject 10 μL of blank.
   Program the data processor to inhibit the peaks due to blank.
   Inject 10 μL of resolution solution and record the Chromatogram.
   Keep the data processor in Area Percent mode and inject 10 μL of blank.
   Inject 10 μL of the sample solution and record the Chromatogram.
   Inject 10 μL of resolution solution and record the Chromatogram.
   System Suitability:
   Resolution between two peaks in the resolution preparation should not be less than 1.5. Requirement: R-Isomer should not be more than 0.1%.

The compound racemic dapoxetine and dapoxetine S(+) enantiomer used herein as a starting material can be in any form, including crude residue or residue resulting from any synthetic processes known in the art. Illustratively, U.S. Pat. No. 5,135,947 is incorporated in its entirety herein for reference.

In yet a still further embodiment, the present invention relates to the use of solid racemic dapoxetine and solid dapoxetine S(+) enantiomer in the synthesis of substantially optically pure dapoxetine or a pharmaceutically acceptable salt thereof.

In yet a still further aspect, the present invention relates to pharmaceutical compositions comprising substantially optically pure dapoxetine or a pharmaceutically acceptable salt thereof and at least a pharmaceutically acceptable excipient.

Such pharmaceutical compositions may be administered to male patients for the treatment of premature ejaculation in adult males and other psychiatric disorders in a dosage form, e.g., solid, liquid, powder, elixir, aerosol, syrups, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, syrup, troches, sachets, suspensions, powders, lozenges, elixirs and the like. Tablets and powders may also be coated with an enteric coating. The enteric-coated powder forms may have coatings containing at least phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, the coating agents may be employed with suitable plasticizers and/or extending agents. A coated capsule or tablet may have a coating on the surface thereof or may be a capsule or tablet comprising a powder or granules with an enteric-coating.

Having described the invention with reference to certain preferred embodiments, other embodiments will become apparent to one skilled in the art from consideration of the specification. The invention is further defined by reference to the following examples describing in detail the preparation of the compound of the present invention. It will be apparent to those skilled in the art that many modifications, both to materials and methods, may be practiced without departing from the scope of the invention.

REFERENCE EXAMPLES

Reference Example 1

50 gms of 1-phenyl,3-napthyloxy 1-propanol, 375 ml of tetrahydrofuran (THF)), 5 mg of dimethylamino pyridine (DMAP) and 60 ml of triethyl amine) were charged in a clean and dry R.B. flask. The reaction mixture was cooled to −5 to 0° C. and a mixture of methane sulfonyl chloride (33 gm) and tetrahydrofuran (125 ml) was added. The resultant reaction mixture was stirred at about 0 to 5° C. for 6 hours and then dimethylamine gas was passed into the reaction mass. The temperature of the reaction mass was raised to room temperature and stirred for about 40 hours. After the completion of the reaction as determined by TLC, the reaction mass was quenched by pouring into chilled water (500 ml) slowly and the pH was adjusted to 0.5 to 1 with concentrated hydrochloric acid. 250 ml of toluene (250 ml) was added and stirred for 30 minutes. The layers were separated and the aqueous layer pH was adjusted to 9 to 10 with 5% w/v sodium hydroxide solution. The aqueous layer extracted with methylene dichloride (4×300 ml) and the solvent distilled off completely to obtain a residue. 100 ml of Ethyl acetate was added to the residue obtained and the mixture was stirred for about 30 minutes, filtered through celite and washed with ethyl acetate. The filtrate was distilled off completely to obtain 47 gm of racemic dapoxetine as a residual oil.

Purity by HPLC: 92 area %.

Reference Example 2

50 gms of (+)-dapoxetine tartrate, 250 ml of methylene dichloride and 250 ml of water were charged into clean and dry R.B. flask and 100 ml of 10% w/v sodium hydroxide solution was added under stirring. The organic layer was separated and the aqueous layer was extracted with 250 ml of methylene dichloride. The combined organic layer was washed with 250 ml of water and the solvent was distilled off completely to obtain 29 gm of dapoxetine S-enantiomer as a residual oil.

Purity by Chiral HPLC: 94% ee.

EXAMPLES

Example 1

Preparation of Solid Racemic Dapoxetine 10 gms of racemic dapoxetine residue as obtained in reference example 1 and 25 ml of n-hexane were charged into a clean and dry R.B. flask and heated to about to reflux. The resultant reaction solution obtained was cooled to 0-5° C. for 1 hour. The precipitated solid racemic dapoxetine was filtered and the solid obtained was washed with precooled n-hexane. The solid was dried at about 40° C. under reduced pressure to afford 7 gms of solid racemic dapoxetine.

Purity by HPLC: 99.5 area %.

The solid racemic dapoxetine was characterized by XRPD, DSC and is substantially as depicted in FIGS. 1 and 2 respectively.

Example 2

Preparation of Solid Racemic Dapoxetine 10 gms of racemic dapoxetine residue and 20 ml of cyclohexane were charged into a clean and dry R.B. flask and heated to reflux. The resultant reaction solution obtained was cooled to 0-5° C. for 2 hours. The precipitated solid racemic dapoxetine was filtered, and the solid was washed with precooled cyclohexane. The solid obtained was dried under reduced pressure to afford 6.5 gm of solid racemic dapoxetine.

Purity by HPLC: 99.5 area %.

Example 3

Preparation of Solid Dapoxetine S-Enantiomer 10 gms of dapoxetine S-enantiomer as obtained in reference example 2 and 25 ml of n-hexane were charged into a clean and dry R.B. flask and heated to reflux. The resultant reaction solution was cooled to 0-5° C. for 1 hour. The precipitated solid dapoxetine S-enantiomer was filtered and the solid was washed with precooled n-hexane. The solid obtained was dried under reduced pressure to afford 8.5 gm of solid dapoxetine S-enantiomer.

Purity by HPLC: 99.4 area %; Purity by Chiral HPLC: 99.9% ee.

The solid racemic dapoxetine was characterized by XRPD, DSC and is substantially as depicted in FIGS. 3 and 4 respectively.

Example 4

Preparation of Solid Dapoxetine S-Enantiomer 10 gms of dapoxetine S-enantiomer and 20 ml of cyclohexane were charged into a clean and dry R.B. flask and heated to reflux. The resultant reaction solution was cooled to 0-5° C. for 2 hours. The precipitated solid dapoxetine S-enantiomer was filtered and the solid was washed with precooled cyclohexane. The solid obtained was dried under reduced pressure to afford 7 gm of solid dapoxetine S-enantiomer.

Purity by HPLC: 99.2 area %; Purity by Chiral HPLC: 99.8%. ee.

We claim:
1. A solid racemic dapoxetine.
2. A process for preparing solid racemic dapoxetine comprising:
   a) providing a solution of racemic dapoxetine in a solvent selected from n-hexane or cyclohexane or a mixture thereof; and
   b) evaporating the solvent(s), or by cooling the solution obtained in step (a) to below about 30° C. to obtain a solid; and
   c) recovering the solid obtained in step (b) by conventional methods to afford the desired racemic dapoxetine.
3. The process of claim 2, wherein the solution in step (a) is obtained by dissolving an oily residue or crude form of racemic dapoxetine or racemic dapoxetine obtained from a reaction mixture of racemic dapoxetine or a salt thereof in a solvent(s) selected from n-hexane or cyclohexane or a mixture thereof.
4. The process of claim 2, wherein the solution of step (a) is obtained at a temperature range from about 30° C. to about the boiling point of the solvent (s) used.
5. The process of claim 2, wherein the solid racemic dapoxetine obtained is dried at a temperature range from about 25° C. to about 45° C. under reduced pressure.
6. The process of claim 2, wherein the solid racemic dapoxetine obtained is optionally recrystallized from a solvent or a mixture of solvents selected from the group consisting of esters, alcohols, or alcohols in combination with water in any proportion.
7. A solid dapoxetine S(+) enantiomer having a purity greater than about 99% as measured by HPLC and greater than about 99.8% e.e. by chiral HPLC.
8. A process for preparing solid dapoxetine S(+) enantiomer comprising:
   a) providing a solution of dapoxetine S(+)-enantiomer in a hydrocarbon solvent selected from n-hexane or cyclohexane or a mixture thereof; and
   b) evaporating the solvent(s) or by cooling the solution obtained in step (a) to below about 30° C.; and
   c) recovering the solid obtained in step (b) by conventional methods to afford the desired solid dapoxetine S(+) enantiomer.
9. The process of claim 8, wherein the solution in step (a) is obtained by dissolving oily residue or crude form of dapoxetine S(+) enantiomer or the dapoxetine S(+) enantiomer obtained from a reaction mixture of dapoxetine S(+)-enantiomer or a salt thereof in a suitable organic solvent selected from n-hexane or cyclohexane or mixtures thereof.
10. The process of claim 8, wherein the solution in step (a) is obtained at a temperature range from about 30° C. to about the boiling point of the solvent(s) used.
11. The process of claim 8, wherein the recovery of solid dapoxetine S(+)enantiomer in step c) is by conventional methods of filtration or centrifugation.
12. The process of claim 8, wherein the solid dapoxetine S(+) enantiomer obtained is dried at temperature range from about 25° C. to about 45° C. under reduced pressure.
13. The process of claim 8, wherein the solid dapoxetine S(+) enantiomer obtained is optionally recrystallized from a solvent or a mixture of solvents selected from the group consisting of esters, alcohols, or alcohols in combination with water in any proportion.
14. The compound of claim 1, having a purity greater than 99.8 area % by HPLC.
15. The process of claim 4, wherein the solution is obtained at a temperature range that is at the boiling point of the solvents used.
16. The process of claim 5, wherein the solid racemic dapoxetine obtained is dried at a temperature range from about 30° C. to about 40° C. under reduced pressure.
17. The process of claim 6, wherein the solid racemic dapoxetine obtained is optionally recrystallized from a solvent or a mixture of solvents which is an ester selected from the group consisting of ethyl acetate and butyl acetate.
18. The process of claim 6, wherein the solid racemic dapoxetine obtained is optionally recrystallized from a solvent or a mixture of solvents which is an alcohol selected from the group consisting of methanol, ethanol, and isopropanol.
19. The process of claim 10, wherein the temperature is at the boiling point of the solvent(s) used.
20. The process of claim 12, wherein the solid dapoxetine S(+) enantiomer obtained is dried at temperature range from about 30° C. to about 40° C. under reduced pressure.
21. The process of claim 13, wherein the solvent or mixture of solvents is an ester selected from the group consisting of ethyl acetate, and butyl acetate.
22. The process of claim 13, wherein the solvent or mixture of solvents is an alcohol selected from the group consisting of methanol, ethanol, and isopropanol.
23. The compound of claim 1, having a purity greater than 99.95 area % by HPLC.
24. The compound of claim 7, having a purity greater than 99.9% e.e by chiral HPLC.

* * * * *